United States Patent
Ogawa

(10) Patent No.: US 10,036,714 B2
(45) Date of Patent: Jul. 31, 2018

(54) IMAGE CAPTURING DEVICE AND INSPECTION APPARATUS AND INSPECTION METHOD

(71) Applicant: NuFlare Technology, Inc., Yokohama (JP)

(72) Inventor: Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 849 days.

(21) Appl. No.: 14/468,605

(22) Filed: Aug. 26, 2014

(65) Prior Publication Data
US 2015/0054941 A1    Feb. 26, 2015

(30) Foreign Application Priority Data

Aug. 26, 2013  (JP) .............................. 2013-175093

(51) Int. Cl.
| | | |
|---|---|---|
| *H04N 7/18* | (2006.01) | |
| *G01N 21/95* | (2006.01) | |
| *G01N 21/88* | (2006.01) | |
| *G01N 21/21* | (2006.01) | |

(52) U.S. Cl.
CPC ......... *G01N 21/9501* (2013.01); *G01N 21/21* (2013.01); *G01N 21/8806* (2013.01); *G01N 2021/8848* (2013.01); *G01N 2201/06113* (2013.01)

(58) Field of Classification Search
None
See application file for complete search history.

(56) References Cited

U.S. PATENT DOCUMENTS

| | | | |
|---|---|---|---|
| 5,477,309 A | * | 12/1995 | Ota .......................... G03F 9/70 355/53 |
| 6,539,106 B1 | | 3/2003 | Gallarda et al. |
| 6,690,469 B1 | | 2/2004 | Shibata et al. |

(Continued)

FOREIGN PATENT DOCUMENTS

| | | | | |
|---|---|---|---|---|
| DE | 102012203947 A1 | * | 3/2013 | ............. G01N 21/21 |
| JP | 06-224104 | | 8/1994 | |

(Continued)

OTHER PUBLICATIONS

U.S. Appl. No. 14/177,546, filed Feb. 11, 2014, Riki Ogawa et al.
U.S. Office Action dated Jun. 29, 2017, issued in U.S. Appl. No. 14/153,199.
Japanese Office Action dated Feb. 6, 2018, issued in Japanese Patent Application No. 2014-171011 (with English abstract).

*Primary Examiner* — James M Anderson, II
(74) *Attorney, Agent, or Firm* — Oblon, McClelland, Maier & Neustadt, L.L.P.

(57) ABSTRACT

An image capturing device comprising, a light source configured to emit light having a predetermined wavelength, a polarization beamsplitter configured to receive the light from the light source, a Faraday rotator configured to rotate a polarization plane of the light via the polarization beamsplitter by changing the intensity of the magnetic field, an objective lens configured to illuminate an inspection target with the light transmitted through the Faraday rotator and a sensor configured to capture an optical image of the inspection target by causing the light reflected by the inspection target to be incident through the objective lens, the Faraday rotator, and the polarization beamsplitter.

11 Claims, 10 Drawing Sheets

(56) References Cited

U.S. PATENT DOCUMENTS

| | | |
|---|---|---|
| 2004/0028267 A1 | 2/2004 | Shoham et al. |
| 2004/0125375 A1 | 7/2004 | Some |
| 2004/0223141 A1 | 11/2004 | Rosengaus |
| 2006/0244976 A1 | 11/2006 | Baer et al. |
| 2007/0002344 A1 | 1/2007 | Klassen |
| 2011/0249112 A1 | 10/2011 | Endo |
| 2011/0255770 A1 | 10/2011 | Touya et al. |
| 2012/0274931 A1 | 11/2012 | Otani et al. |
| 2013/0176559 A1 | 7/2013 | Ogawa et al. |
| 2014/0002826 A1 | 1/2014 | Inoue et al. |
| 2014/0043467 A1 | 2/2014 | Yamashita |
| 2014/0055774 A1 | 2/2014 | Sugihara et al. |
| 2014/0055780 A1 | 2/2014 | Ogawa et al. |
| 2014/0072202 A1 | 3/2014 | Ogawa et al. |
| 2014/0104412 A1 | 4/2014 | Inoue et al. |
| 2014/0111636 A1 | 4/2014 | Inoue et al. |
| 2014/0204202 A1 | 7/2014 | Ogawa et al. |
| 2014/0232849 A1 | 11/2014 | Ogawa et al. |

FOREIGN PATENT DOCUMENTS

| | | |
|---|---|---|
| JP | 2001-208697 A | 8/2001 |
| JP | 2002-221495 A | 8/2002 |
| JP | 2003-042967 A | 2/2003 |
| JP | 2006-47308 A | 2/2006 |
| JP | 2006-512588 A | 4/2006 |
| JP | 2007-225341 A | 9/2007 |
| JP | 4236825 | 3/2009 |
| JP | 2009-192520 A | 8/2009 |
| JP | 2009-198396 | 9/2009 |
| JP | 2012-127856 A | 7/2012 |
| JP | 2012-185178 A | 9/2012 |
| JP | 2014-137358 A | 7/2014 |
| WO | WO 2010/050488 A1 | 5/2010 |

\* cited by examiner

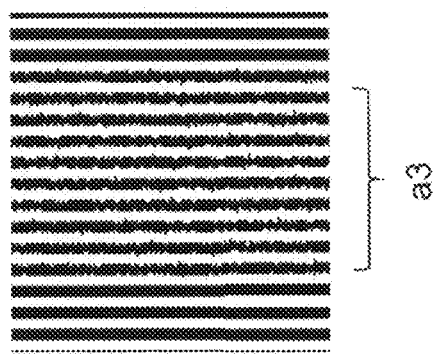
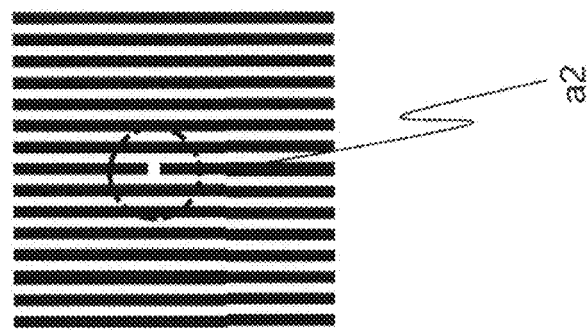
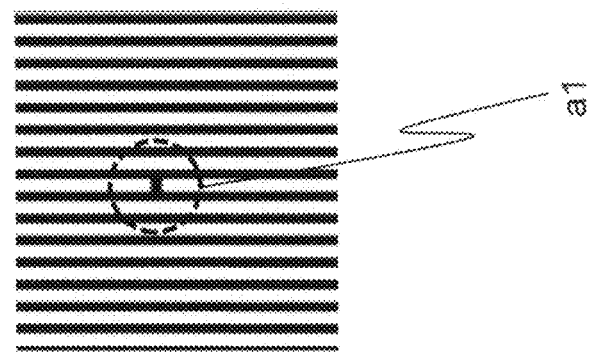

IMAGE CAPTURING DEVICE AND INSPECTION APPARATUS AND INSPECTION METHOD

CROSS-REFERENCE TO THE RELATED APPLICATION

The entire disclosure of the Japanese Patent Application No. 2013-175093, filed on Aug. 26, 2013 including specification, claims, drawings, and summary, on which the Convention priority of the present application is based, are incorporated herein in its entirety.

FIELD OF THE INVENTION

The present invention relates to an Image Capturing Device and an Inspection Apparatus and Inspection Method.

BACKGROUND

Recently, with increasing integration degree of a semiconductor device, dimensions of individual element become finer, and widths of wiring and gate constituting each element also become finer.

A process of transferring an original plate (a mask or a reticle, hereinafter collectively referred to as a mask) to a photosensitive resin to fabricate a wafer is fundamental to production of a semiconductor integrated circuit. The semiconductor integrated circuit is produced by repeating the fundamental process.

An exposure apparatus called a stepper or a scanner is used in the transfer process. In the exposure apparatus, light is used as a transfer light source, and a circuit pattern on the reticle is projected onto the wafer while reduced to about one-fourth to about one-fifth. In order to increase the integration degree of the semiconductor integrated circuit, it is necessary to improve resolution performance in the transfer process. If NA is a numerical aperture of an imaging optical system, and $\lambda$ is a wavelength of the light source, a resolution dimension is proportional to ($\lambda$/NA). Accordingly, higher exposure resolution can be achieved by increasing the numerical aperture NA or decreasing the wavelength $\lambda$.

As another example for the higher exposure resolution, nanoimprint lithography (NIL) has attracted attention as a technology for forming the fine pattern. In the nanoimprint lithography, a fine pattern is formed in a resist by pressuring a master template (a mold) having a nanometer-scale fine structure to the resist on the wafer. In the nanoimprint technology, in order to enhance productivity, plural duplicate templates (replica templates) are produced using a master template that is an original plate, and then the replica templates are attached to and used in each nanoimprint lithography apparatuses.

It is necessary to improve a production yield of the expensive LSI in a production process. A defect of a circuit pattern formed on of a mask or template can be cited as a large factor that reduces a production yield of the semiconductor element. It is necessary to detect the shape defect of the extremely small pattern in a mask inspection process. Japanese Patent Number 4236825 discloses an inspection apparatus that can detect fine defects in the mask.

In the mask inspection process, the mask is illuminated with the light while the mask is moved with a mask stage, and the pattern formed on the mask is imaged with an imaging element such as a CCD camera. Then, an obtained optical image is compared to a reference image, namely, an image that is compared to the optical image of a pattern in order to detect a defect, and a place where a difference between the optical image and the reference image exceeds a threshold is detected as a defect. The difference, for example, can be caused by short defects or open defects.

In the inspection, it is necessary to sufficiently ensure a quantity of light incident to the sensor. A shortage of the light quantity causes degradation of inspection accuracy and lengthening of inspection time. In a reflected illumination optical system, light emitted from a light source is reflected by a half mirror, a mask is irradiated with the light, the light reflected by the mask is transmitted through the half mirror, and the light is incident to a sensor to capture an optical image. At this point, only the light reflected by the half mirror is used as the illumination light for the mask, which decreases the light quantity to a half of the quantity of light emitted from the light source. Then, only the light transmitted through the half mirror in the light reflected from the mask is used as the light incident to the sensor, which further decreases the light quantity to a half again. That is, in the reflecting optical system, the light incident to the sensor becomes a quarter of the quantity of light emitted from the light source.

Therefore, there is a demand for an image capturing device that can capture an image of a mask pattern while minimally restraining the degradation of the light emitted from the light source in the reflected illumination optical system, and inspection apparatus or an inspection method. The invention has been devised to solve the problem described above. An object of the invention is to provide an image capturing device that can minimally restrain the degradation of the light quantity in the reflected illumination optical system to capture an image of a target. Another object of the invention is to provide an inspection apparatus and an inspection method, for being able to minimally restrain the degradation of the light quantity in the reflected illumination optical system to perform high-accuracy inspection.

Other advantages and challenges of the present invention are apparent from the following description.

SUMMARY OF THE INVENTION

According to one aspect of the present invention, an image capturing device comprising, a light source configured to emit light having a predetermined wavelength, a polarization beamsplitter configured to reflect the light from the light source, a Faraday rotator having a optical material configured to rotate a polarization plane of the light reflected from the polarization beamsplitter by changing intensity of a magnetic field or changing the thickness of the optical material, an objective lens configured to illuminate an inspection target with the light transmitted through the Faraday rotator and a sensor configured to capture an optical image of the inspection target by causing the light reflected by the inspection target to be incident through the objective lens, the Faraday rotator, and the polarization beamsplitter.

Further to this aspect of the present invention, an image capturing device, wherein the Faraday rotator rotates a polarization plane of the light before the transmission through the Faraday rotator such that the polarization plane rotates 90 degrees by transmitting the light back and forth through the Faraday rotator, by applying the magnetic field.

Further to this aspect of the present invention, an image capturing device, wherein the Faraday rotator includes an optical material that transmits the light, and the magnetic field is applied to the optical material by one selected from a group consisting of an electromagnet, a permanent magnet, and a combination of the electromagnet and permanent magnet.

Further to this aspect of the present invention, an image capturing device, further comprising, a half-wavelength plate configured between the polarization beamsplitter and the inspection target, wherein the half-wavelength plate changes a polarization direction of the light with which the inspection target is illuminated.

Further to this aspect of the present invention, an image capturing device, wherein the half-wavelength plate is configured between the polarization beamsplitter and the Faraday rotator.

Further to this aspect of the present invention, an image capturing device, wherein the half-wavelength plate is configured between the Faraday rotator and the inspection target.

Further to this aspect of the present invention, an image capturing device, wherein the half-wavelength plate includes a rotation mechanism, and the rotation mechanism changes the polarization direction of the light by changing an angle of the half-wavelength plate.

Further to this aspect of the present invention, an image capturing device, wherein the predetermined wavelength of the light from the light source and a numerical aperture of an objective lens defines a resolution limit, wherein the resolution limit is a value at which a repetitive pattern formed in the inspection target is not resolved.

Further to this aspect of the present invention, an image capturing device comprising, an image processor configured to obtain a gradation value in each pixel with respect to the optical image and acquire
(1) a rotation angle of the polarization plane of the light rotated by the Faraday rotator for minimizing a standard deviation of the gradation value, or
(2) a rotation angle for minimizing a value which is obtained by dividing the standard deviation of the gradation values of a plurality of optical images obtained by changing the rotation angle, by a square root of an average gradation value obtained from the gradation value, an angle controller configured to apply a magnetic field to the Faraday rotator or select the optical materials with proper thickness in the Faraday rotator so as to obtain the rotation angle acquired by the image processor, and a defect detector configured to detect a defect of the sample based on an optical image which is captured while the magnetic field is applied to the Faraday rotator.

In another aspect of the present invention, an inspection apparatus comprising, an illumination optical system including a light source configured to emit light having a predetermined wavelength, a polarization beamsplitter configured to reflect the light emitted from the light source, a half-wavelength plate and a Faraday rotator configured between the polarization beamsplitter and a sample which is an inspection target, configured to transmit the light reflected by the polarization beamsplitter, wherein the illumination optical system is configured to illuminate the sample by the light including a polarization plane having an angle except an angle within a range of −5 degrees to 5 degrees and a range of 85 degrees to 95 degrees with respect to a repetitive direction of a repetitive pattern formed in the sample, a sensor that captures an optical image of a pattern formed in the sample, an imaging optical system that forms an image of the light reflected by the sample onto the sensor by causing the light to be transmitted through the Faraday rotator, the half-wavelength plate, and the polarization beamsplitter.

Further to this aspect of the present invention, an inspection apparatus, wherein the half-wavelength plate is configured between the polarization beamsplitter and the Faraday rotator.

Further to this aspect of the present invention, an inspection apparatus, wherein the half-wavelength plate is configured between the Faraday rotator and the sample.

Further to this aspect of the present invention, an inspection apparatus comprising, an image processor configured to obtain a gradation value in each pixel with respect to the optical image and to acquire
(1) a rotation angle of the polarization plane of the light rotated by the Faraday rotator for minimizing a standard deviation of the gradation value, or
(2) a rotation angle for minimizing a value which is obtained by dividing the standard deviation of the gradation values of a plurality of optical images obtained by changing the rotation angle, by a square root of an average gradation value obtained from the gradation value, an angle controller that applies a magnetic field to the Faraday rotator or select the optical material with proper thickness in the Faraday rotator so as to obtain the rotation angle acquired by the image processor, and a defect detector that detects a defect of the sample based on an optical image which is captured while the magnetic field is applied to the Faraday rotator or the optical material with proper thickness in the Faraday rotator is selected.

Further to this aspect of the present invention, the inspection apparatus, wherein the predetermined wavelength of the light from the light source and a numerical aperture of an objective lens through which the sample is illuminated with the light transmitted through the Faraday rotator defines a resolution limit, wherein the resolution limit is a value at which the pattern is not resolved.

Further to this aspect of the present invention, the inspection apparatus, wherein the Faraday rotator includes an optical material that transmits the light, and the magnetic field is applied to the optical material by one selected from a group consisting of an electromagnet, a permanent magnet, and a combination of the electromagnet and permanent magnet.

In another aspect of the present invention, an inspection method comprising, reflecting light emitted from the light source which emits the light having a predetermined wavelength by a polarization beamsplitter, transmitting the light through a half-wavelength plate and a Faraday rotator, forming the light including a polarization plane having an angle except an angle within a range of −5 degrees to 5 degrees and a range of 85 degrees to 95 degrees with respect to a repetitive direction of a repetitive pattern formed in a sample which is an inspection target, converging the light transmitted through the Faraday rotator by an objective lens to be illuminated the sample, transmitting the light reflected by the sample through the Faraday rotator, the half-wavelength plate, and the polarization beamsplitter, imaging the light on a sensor to capture an optical image of a pattern formed in the sample, obtaining a gradation value in each pixel with respect to the optical image, acquiring (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images obtained by changing the rotation angle, by a square root of an average gradation value obtained from the gradation value, applying a magnetic field to the Faraday rotator or selecting the optical material with proper thickness in the Faraday rotator such that the acquired rotation angle is obtained, and detecting a defect of the sample based on the optical image which is captured while the magnetic field is applied to the Faraday rotator or the optical material with proper thickness in the Faraday rotator is selected.

Further to this aspect of the present invention, an inspection method, wherein the predetermined wavelength of the light from the light source and a numerical aperture of an objective lens defines a resolution limit, wherein the resolution limit is a value at which a repetitive pattern formed in the inspection target is not resolved.

Further to this aspect of the present invention, an inspection method, wherein the Faraday rotator includes an optical material that transmits the light, and the application of the magnetic field to the Faraday rotator is the application of the magnetic field to the optical material by one selected from a group consisting of an electromagnet, a permanent magnet, and a combination of the electromagnet and permanent magnet.

Further to this aspect of the present invention, an inspection method, wherein the application of the magnetic field to the Faraday rotator is the application of the magnetic field to the optical material by one selected from a plurality of permanent magnets having different intensities of the magnetic field.

Further to this aspect of the present invention, an inspection method, wherein the application of the magnetic field to the Faraday rotator is the application of the magnetic field to an optical material after the optical material implementing the acquired rotation angle is selected from a plurality of optical materials constituting a component of the Faraday rotator with different thicknesses.

BRIEF DESCRIPTION OF THE DRAWINGS

FIG. 6 schematically illustrates an example of the short-circuit defect.

FIG. 7 schematically illustrates an example of the open-circuit defect.

FIG. 8 schematically illustrates a defect caused by edge roughness.

DETAILED DESCRIPTION OF THE EMBODIMENTS

Figure 1:
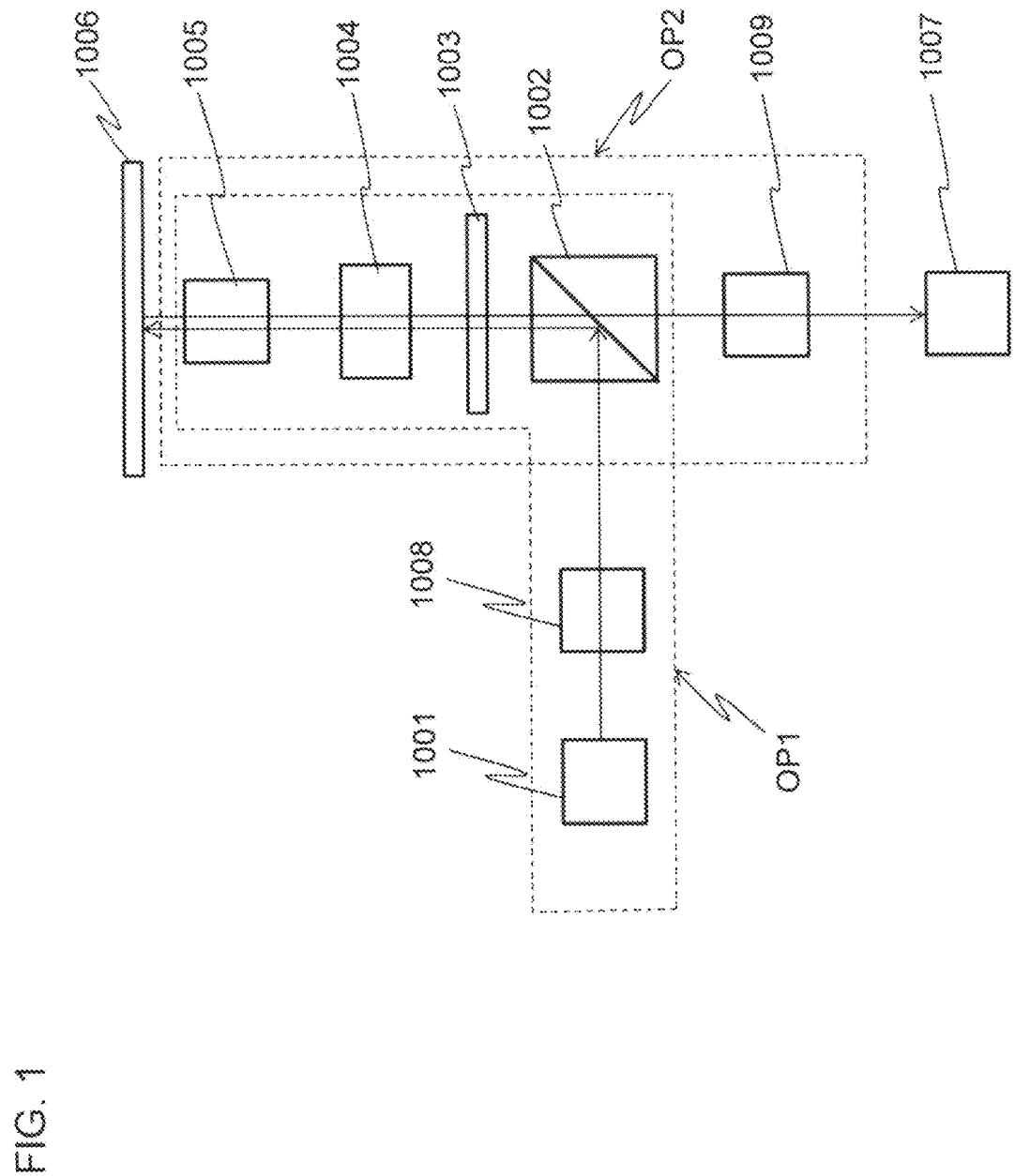
FIG. 1 illustrates an example of a configuration of an image capturing device according to the present embodiment.

FIG. 1 illustrates an example of a configuration of an image capturing device according to the present embodiment. The image capturing device includes an illumination optical system OP1 that illuminates a mask 1006, a sensor 1007 that captures an image of a pattern of the mask 1006, and an imaging optical system OP2 that images the light reflected from the mask 1006 onto the sensor 1007.

The illumination optical system OP1 includes a light source 1001, a beam shaping optical system 1008, a polarization beamsplitter 1002, a half-wavelength plate 1003, a Faraday rotator 1004, and an objective lens 1005. The beam shaping optical system 1008 includes an expander lens that expands a beam, an integrator lens that increases the uniformity of the light to the surface, and a relay lens in which a magnification is set such that a mask surface is illuminated with the beam at a desired size. On the other hand, the imaging optical system OP2 includes the objective lens 1005, the Faraday rotator 1004, the half-wavelength plate 1003, the polarization beamsplitter 1002, and an imaging optical system 1009. The polarization beamsplitter 1002, the half-wavelength plate 1003, the Faraday rotator 1004, and the objective lens 1005 are shared by the illumination optical system OP1 and the imaging optical system OP2. The imaging optical system 1009 includes a lens group that images the mask onto a sensor surface with the desired magnification.

A laser light source can be used as the light source 1001 in FIG. 1. The light source that emits DUV (Deep Ultraviolet Radiation) light is preferably used in the present embodiment. This enables the inspection to be performed without generating the throughput degradation that becomes troublesome when an EB (Electron Beam) is used as the light source.

Generally the light emitted from the laser light source is linearly-polarized light. In the present embodiment, the inspection is performed while the mask 1006 that is an inspection target is illuminated with the linearly-polarized light.

In the illumination optical system OP1 in FIG. 1, the linearly-polarized light emitted from the light source 1001 is reflected by the polarization beamsplitter 1002, and is incident to the Faraday rotator 1004 through the half-wavelength plate 1003.

Figure 2:
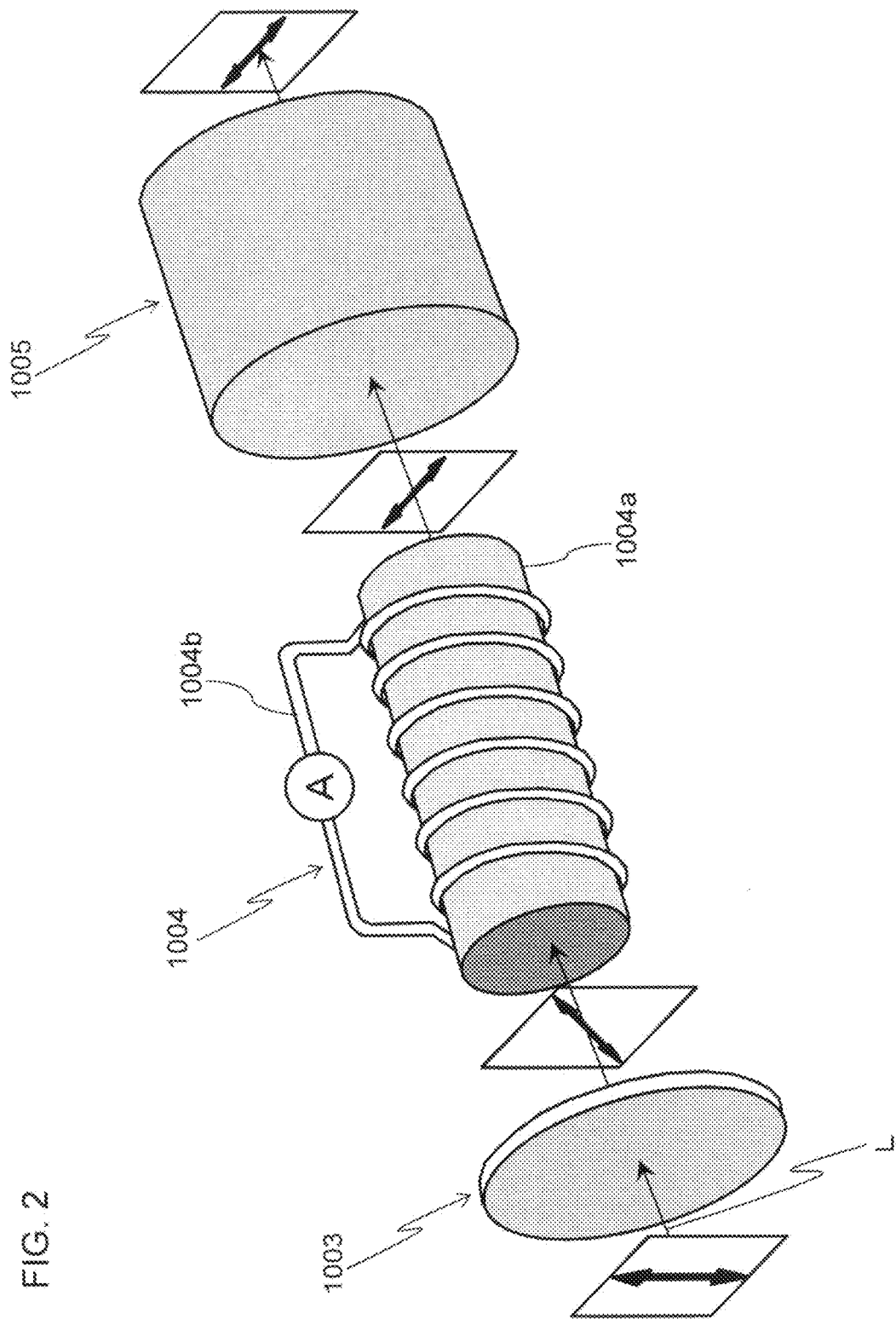
FIG. 2 illustrates a state in which the polarization plane of the light rotates.

As illustrated in FIG. 2, the Faraday rotator 1004 includes an optical material 1004a that transmits the light and a coil 1004b that is wound around the optical material 1004a. A material having high transmittance to the light emitted from the light source 1001 is used as the optical material 1004a. For example, in the case that the light source 1001 emits the DUV light, a material, such as $SiO_2$, $CaF_2$, and $MgF_2$, which has the transmittance to ultraviolet light, is used as the optical material 1004a. The coil 1004b is wound such that passage of a current applies a magnetic field to the optical material 1004a in a direction parallel to a traveling direction of the light.

The Faraday rotator 1004 rotates a polarization plane of the light by a Faraday effect. As used herein, the Faraday effect means a phenomenon in which, when the linearly-polarized light is incident to an optical material to apply the magnetic field in the same direction as the traveling direction of the light, a deviation is generated between phase velocities of two components (right-handed circularly-polarized light and left-handed circularly-polarized light) of the linearly-polarized light, and therefore the polarization plane of the light (linearly-polarized light) outgoing from the optical material rotates by a phase difference at an exit of the Faraday rotator 1004, that is, the exit of the light incident into the Faraday rotator.

Figure 3:
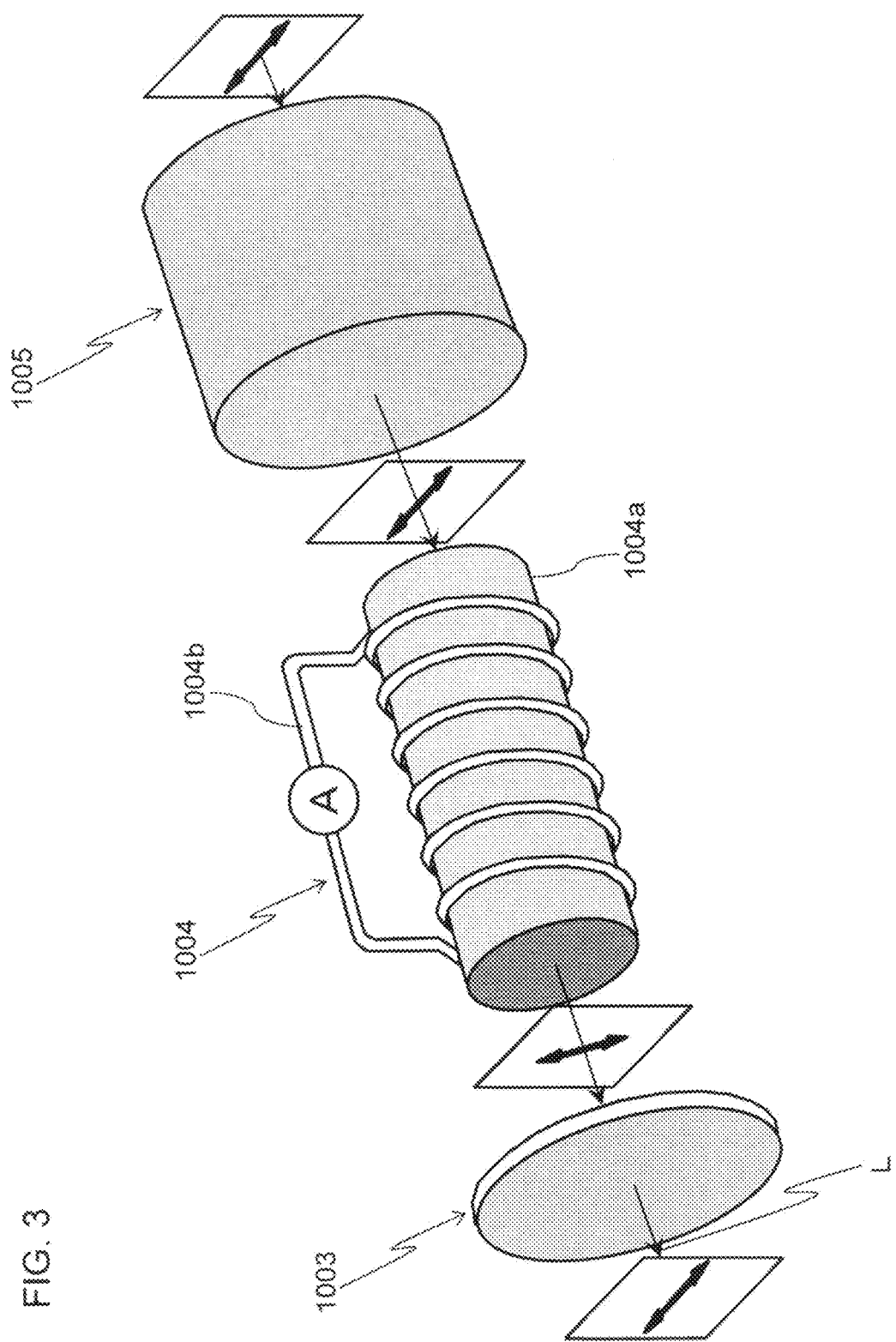
FIG. 3 illustrates a state in which the polarization plane of the light rotates.

In the present embodiment, preferably the polarization plane of the light rotates by 90 degrees as a result of transmitting back and forth through the Faraday rotator 1004. That is, preferably the magnetic field is applied to the optical material such that polarization plane of the light rotates by 90 degrees as a result of transmitting back and forth. FIGS. 2 and 3 illustrate a state in which the polarization plane of the light rotates. In FIGS. 2 and 3, the same components are designated by the same numerals as that in FIG. 1.

In the example of FIG. 2, a linearly-polarized light L is transmitted through the half-wavelength plate 1003, whereby the polarization plane of the linearly-polarized light L rotates by 45 degrees. Then, the linearly-polarized light L is transmitted through the Faraday rotator 1004, whereby the polarization plane of the linearly-polarized light L further rotates by 45 degrees. Then, the linearly-polarized light L is imaged on the mask (not illustrated in FIG. 2) through the objective lens 1005.

In FIG. 3, the linearly-polarized light L reflected by the mask (not illustrated in FIG. 3) is incident to the Faraday rotator 1004 through the objective lens 1005. The linearly-polarized light L is transmitted through the Faraday rotator 1004, whereby the polarization plane of the linearly-polarized light L rotates by 45 degrees. Then, the linearly-polarized light L is transmitted through the half-wavelength plate 1003, whereby the polarization plane of the linearly-polarized light L rotates by −45 degrees.

Thus, in the example of FIGS. 2 and 3, the light emitted from the light source 1001 is transmitted through the Faraday rotator 1004 twice, whereby the polarization direction of the light rotates by 90 degrees. In FIG. 1, the light emitted from the light source 1001 is reflected by the polarization beamsplitter 1002 and travels toward the mask 1006, and the polarization direction of the light reflected by the mask 1006 rotates by 90 degrees. Therefore, the light is transmitted through the polarization beamsplitter 1002, and travels toward the sensor 1007, not the light source 1001. When the light is incident to the sensor 1007, the sensor 1007 captures the optical image of the mask 1006.

The polarization direction of the light with which the mask 1006 is illuminated changes by both the Faraday rotator 1004 and the half-wavelength plate 1003. At this point, the Faraday rotator 1004 can change an angle of the polarization direction of the light by changing an intensity of the magnetic field applied to the optical material. On the other hand, a rotation mechanism is provided in the half-wavelength plate 1003 to be able to arbitrarily change the rotation angle.

As an example of the Faraday rotator, the magnetic field is applied to the optical material by passing the current through the coil. However, the Faraday rotator is not limited to one in which the electromagnet is used, but a permanent magnet or a combination of the electromagnet and the permanent magnet may be used in the Faraday rotator. An optical refractive index changes substantially linearly according to a temperature. Therefore, in the electromagnet, there is a risk that a temperature distribution is generated in the coil to generate an aberration. On the other hand, the problem can be avoided in the case that the permanent magnet is used. In this case, preferably a type of the permanent magnet or the number of permanent magnets can be varied such that the magnetic field is generated according to the necessary rotation angle. In the combination of the permanent magnet and the electromagnet, the permanent magnet is provided to generate the basic magnetic field, and the magnetic field necessary to generate the necessary rotation angle can be generated by the electromagnet. In this configuration, necessity to exchange the permanent magnet is eliminated, and a temperature rise can minimally be restrained.

Figure 4:
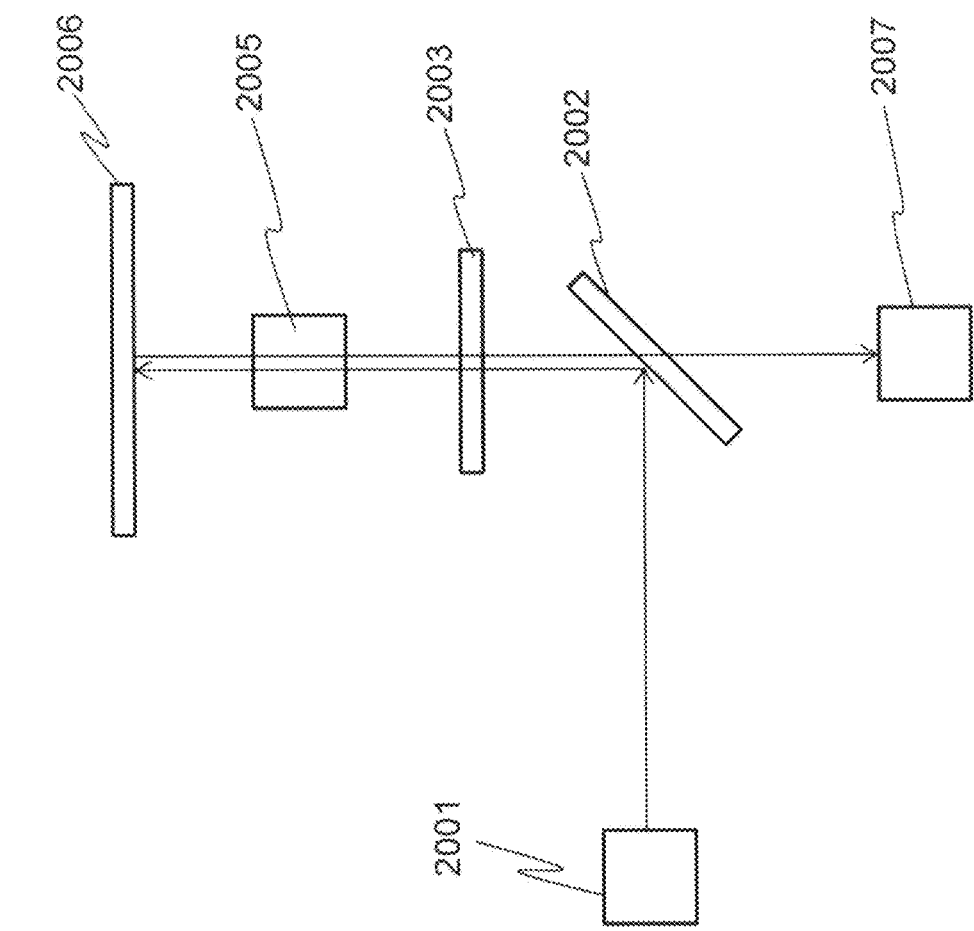
FIG. 4 illustrates an example of an image capturing device that is a comparative example of the present embodiment.

FIG. 4 illustrates an example of an image capturing device that is a comparative example of the present embodiment. In the image capturing device of the comparative example, the light emitted from a light source 2001 is reflected by a half mirror 2002, transmitted through a half-wavelength plate 2003, and is incident to a mask 2006 through a light objective lens 2005, and the mask 2006 is illuminated with the light. The light reflected by the mask 2006 is incident to the sensor 2007 through the objective lens 2005, the half-wavelength plate 2003, and the half mirror 2002.

Using the image capturing device having the configuration in FIG. 4, the mask 2006 can be illuminated with the light having a polarization characteristic similar to that in FIG. 1, and the light is incident to the sensor 2007. However, in the configuration in FIG. 4, the light quantity from the light source 2001 is considerably decreased due to a characteristic of the half mirror 2002. That is, the light quantity decreases to a half of the quantity of light emitted from the light source 2001 when only the light reflected by the half mirror 2002 is used as the illumination light for the mask 2006. The light quantity further decreases to a half when only the light transmitted through the half mirror 2002 in the light reflected from the mask 2006 is used as the light incident to the sensor. Accordingly, for the image capturing device in FIG. 4, the light incident to the sensor 2007 becomes a quarter of the quantity of light emitted from the light source 2001.

On the other hand, in the image capturing device of the present embodiment in FIG. 1, the degradation of the light quantity emitted from the light source 1001 can minimally be restrained because the half mirror is not used. Therefore, the light quantity enough to perform the inspection can be incident to the sensor 1007. When the image capturing device of the present embodiment is applied to the inspection apparatus, the inspection accuracy can be improved, and the inspection time can be shortened. The image capturing device can also be applied to applications other than the inspection apparatus.

With the progress of microfabrication of the circuit pattern, a pattern size becomes finer than a resolution of the optical system of the inspection apparatus. For example, when a half pitch of the periodic pattern is smaller than 50 nm, the pattern cannot be resolved by the light source in which the DUV light is used. However, in the image capturing device of the present embodiment shown in FIG. 1, the periodic pattern in which the half pitch is smaller than 50 nm can accurately be inspected. The inspection apparatus of the present embodiment will be described below.

Figure 5:
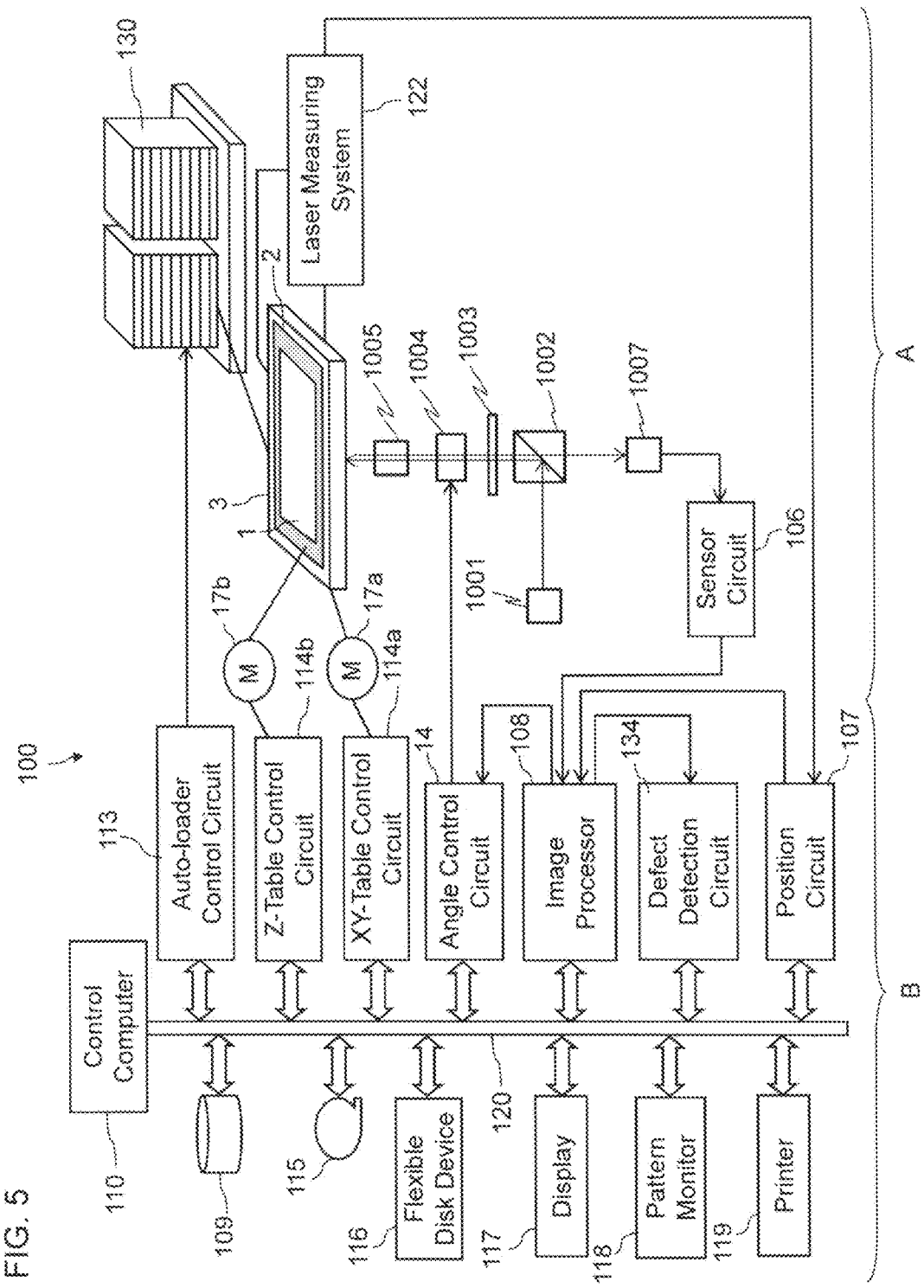
FIG. 5 is a schematic configuration diagram of an inspection apparatus according to the present embodiment.

FIG. 5 is a schematic configuration diagram of an inspection apparatus 100 according to the present embodiment. The inspection apparatus 100 includes an optical unit as shown in FIG. 1. Further, an inspection apparatus 100 includes an optical image acquiring unit A and a control unit B.

Firstly, the optical image acquiring unit A will be described.

In addition to the optical systems in FIG. 1, the optical image generation part A includes a Z-Table 2 that is movable in a vertical direction (Z-direction), an XY-Table 3 that is movable in a horizontal direction (X-direction and Y-direction), a sensor circuit 106, a laser length measuring system 122, and autoloader 130. The XY-Table 3 may have a structure that is movable in the rotation direction.

A sample 1 that is an inspection target is placed on the Z-Table 2. The Z-Table 2 is provided on the XY-Table 3. The mask used in the photolithography technology, and the template used in the nanoimprint technology can be cited as an example of the sample 1.

A repetitive pattern such as a line and space pattern, namely, a regular repetitive pattern having periodicity is formed in the sample 1. At least a part of the pattern is a pattern of an optical resolution limit or less.

A pattern formed in a memory mat of a semiconductor chip can be cited as an example of the pattern of the optical resolution limit or less. As used herein, the resolution limit means a resolution limit of the optical system in the inspection apparatus 100, namely, a resolution limit ($R=\lambda/2NA$) defined by a wavelength ($\lambda$) of the light emitted from the light source 1001 and a numerical aperture (NA) of the objective lens 1005. In the present embodiment, the resolution limit is a value at which at least a part of the pattern formed in the sample 1 is not resolved.

Preferably the sample 1 is supported at three points using support members provided in the Z-Table 2. In the case that the sample 1 is supported at four points, it is necessary to adjust a height of the support member with high accuracy. Unless the height of the support member is sufficiently adjusted, there is a risk of deforming the sample 1. On the other hand, in the three-point support, the sample 1 can be supported while the deformation of the sample 1 is suppressed to the minimum. The supporting member is configured by using a ballpoint having a spherical head surface. For example, the two support members in the three support members are in contact with the sample 1 at two corners, which are not diagonal but adjacent to each other in four corners of the sample 1. The remaining support member in the three support members is disposed in the region between the two corners at which the two other support members are not disposed.

The light source 1001 emits the light to the sample 1 in order to generate the optical image of the sample 1. The beam shaping optical system 1008 performs beam shaping to the light emitted from the light source 1001. After that, the light is reflected by the polarization beamsplitter 1002, transmitted through the half-wavelength plate 1003, and is incident to the Faraday rotator 1004. Then the sample 1 is illuminated with the light transmitted through the Faraday rotator 1004 through the objective lens 1005.

The light reflected by the sample 1 is transmitted through the objective lens 1005, the Faraday rotator 1004, the half-wavelength plate 1003, and the polarization beamsplitter 1002, enlarged with a predetermined magnification by the imaging optical system 1009, and is incident to the sensor 1007. The sensor 1007 captures the optical image of the mask 1.

A short-circuit defect in which lines are short-circuited and an open-circuit defect in which the line is disconnected are detected in a pattern of an optical resolution limit or less. FIG. 6 illustrates an example of the short-circuit defect. In a region a1, two lines adjacent to each other are connected to generate the short-circuit defect. FIG. 7 illustrates an example of the open-circuit defect. In a region a2, the line is partially disconnected. Short-circuit defects and open-circuit defects have a serious influence on the performance of the mask. In FIG. 6 and FIG. 7, the black region is several tens of nm lower than the white region when the mask is a template for nanoimprint lithography (NIL).

As to another example of pattern defect, edge roughness becomes prominent as illustrated in a region a3 as shown in FIG. 8. However, this defect has a restricted influence on the performance of the mask unlike the short-circuit defect and the open-circuit defect. In FIG. 8, the black region is several tens of nm lower than the white region when the mask is a template for nanoimprint lithography (NIL).

Some defects become practically problematic, and some defects do not become practically problematic. Only the defect becoming practically problematic should be detected in the inspection. Specifically, it is necessary to defect the short-circuit defect and the open-circuit defect, but it is not necessary to defect the edge roughness. However, in the case that the short-circuit defect, the open-circuit defect, and the edge roughness having the size of the optical resolution limit or less are mixed in the pattern of the optical resolution limit or less, more particularly the repetitive pattern having a period of the optical resolution limit or less of the optical system in the inspection apparatus, in observation with the optical system, the brightness and darkness caused by the short-circuit defect or the open-circuit defect is not distinguished from the brightness and darkness caused by the edge roughness. This is because, in the optical image of the pattern, all of the defects, that is, the short-circuit defect, the open-circuit defect, and the edge roughness become blurred by the same amount, that is, these defects are expanded to the same size, namely, to about the optical resolution limit of size.

Figure 9:
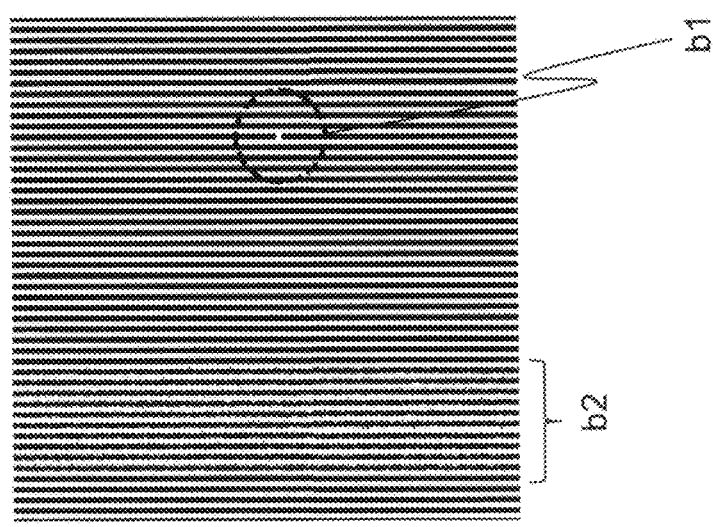
FIG. 9 schematically illustrates the line and space pattern.

FIG. 9 schematically illustrates the line and space pattern provided in the sample that is the inspection target. In FIG. 9, it is assumed that the size of the pattern is smaller than the resolution limit of the optical system. In FIG. 9, the black region is several tens of nm lower than the white region when the mask is a template for nanoimprint lithography (NIL). In the region b1 in FIG. 9, the line pattern is partially lacking thus generating the open-circuit defect. In the region b2, the edge roughness of the line pattern becomes prominent. Although a difference of the defect between the open-circuit defect in the region b1 and the edge roughness in the region b2, is clearly recognized on the actual mask, the differences are hardly distinguished from each other by the observation through the optical system. This is because the optical system behaves as a spatial frequency filter defined by a wavelength $\lambda$ of the light emitted from the light source and a numerical aperture NA.

Figure 10:
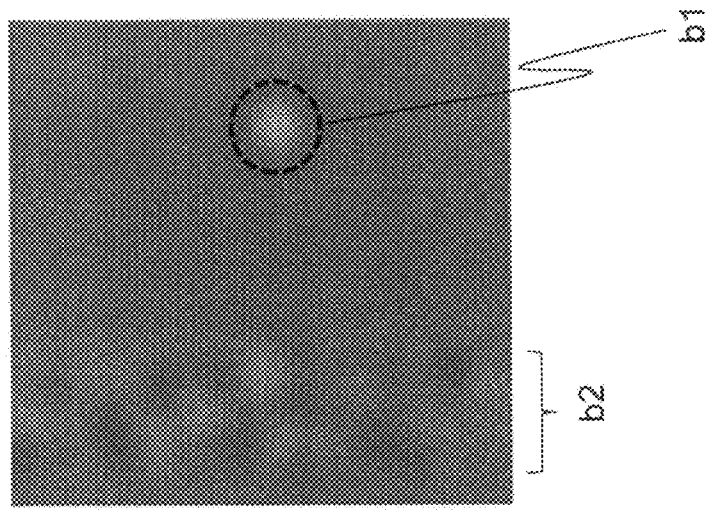
FIG. 10 illustrates a state in which the pattern in FIG. 9 is subjected to the spatial frequency filter.

FIG. 10 illustrates a state in which the pattern in FIG. 9 is subjected to the spatial frequency filter. As can be seen from FIG. 10, the defect in the region b1 and the defect in the region b2 are expanded to the similar size, and the shapes of the defects are hardly distinguishable from each other. Thus, in principle, the open-circuit defect of the optical resolution limit or less and the edge roughness are hardly distinguished from each other by the optical system. The same holds true for the short-circuit defect and the edge roughness.

The large defect such as the short-circuit defect and the open-circuit defect has the large influence on the polarization state of the illumination light compared with the small defect such as the defect caused by the edge roughness. Specifically, in the short-circuit defect in FIG. 6, a vertical direction and a horizontal direction differ from each other in sensitivity for an electric field component of the illumination light when the adjacent lines are connected to each other.

For example, it is considered that the linearly-polarized light is perpendicularly incident to the mask. When the polarization direction of the linearly-polarized light is 45 degrees with respect to a direction along an edge of the line and space pattern, while a vertical component and a horizontal component of an electric field of the incident light are equal to each other, a difference between the horizontal component and the vertical component of the electric field of the reflected light increases due to the open-circuit defect and the short-circuit defect. As a result, the polarization state of the light reflected from the short-circuit defect differs from that of the incident light.

On the other hand, for the defect caused by the edge roughness in FIG. 8, the lines are not connected to each other, and the lines are not disconnected. Because a size of irregularities in the edge roughness is finer than the short-circuit defect and the open-circuit defect, sensitivity between the vertical and horizontal directions of the electric field component of the illumination light is not so large.

Therefore, in the case that the linearly-polarized light is incident to the mask, the polarization direction of the light scattered by the edge roughness becomes a value close to 45 degrees of the polarization direction of the incident light when the linearly-polarized light has the polarization direction of 45 degrees with respect to the direction along the edge of the line and space pattern. However, because the direction of edge roughness depends on the direction of the line and space, the vertical direction and the horizontal direction are not completely equal to each other in sensitivity for the polarization, but the polarization direction of the reflected light changes slightly from 45 degrees.

Figure 12:
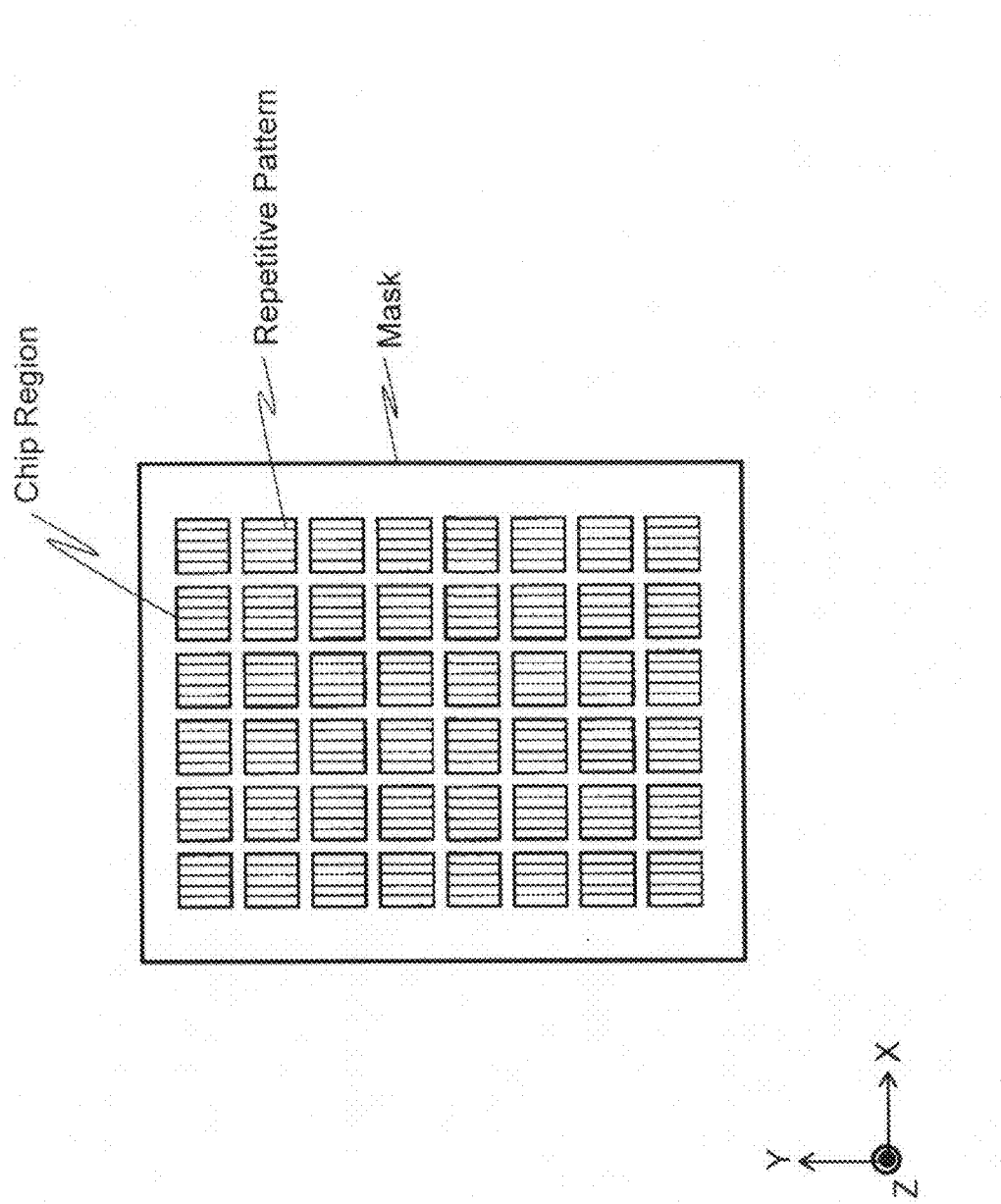
FIG. 12 illustrates a state in which multiple chip regions are arrayed along the X-direction and the Y-direction on a mask.

FIG. 12 illustrates an example in which multiple chip regions are arrayed in the X-direction and the Y-direction. The repetitive pattern is formed in each chip region. For example, the repetitive pattern is a wiring pattern such as the line and space pattern, specifically the pattern in which multiple line portions are arrayed at constant intervals along the X-direction. In this case, the array direction (X-direction) of the line portion is referred to as "a repetitive direction of a repetitive pattern".

In the present embodiment, preferably the polarization direction of the incident light has the angle of 45 degrees with respect to the repetitive direction of the repetitive pattern formed in the mask.

When the polarization direction of the incident light is 45 degrees with respect to the repetitive direction of the repetitive pattern, the vertical component and the horizontal component of the electric field of the incident light are equal to each other. On the other hand, the horizontal component is larger than the vertical component in the electric field of the reflected light due to the short-circuit defect in which the line portions short-circuited to each other. As a result, the polarization direction of the light reflected from the short-circuit defect is inclined in the repetitive direction of the repetitive pattern. For the open-circuit defect in which the line portion is disconnected, the polarization direction of the light is inclined in the direction orthogonal to the repetitive direction of the repetitive pattern.

The short-circuit defect or the open-circuit defect differs from the edge roughness in the influence on the polarization state of the illumination light. Accordingly, even if the pattern has the optical resolution limit or less of the optical system, the defect can be classified by taking advantage of the difference. Specifically, by controlling the polarization state of the illumination light and the condition for the polarization control element in the optical system that images the light reflected from the mask, the bright and dark unevenness caused by the edge roughness can be removed with the polarization control element to extract only the change in amplitude of the short-circuit defect or open-circuit defect.

Specifically, in FIG. 5, the rotation angle (Faraday rotation angle $\theta$) of the polarization plane of the light is changed in the Faraday rotator 1004 such that the light scattered by the edge roughness of the sample 1 is reflected by the polarization beamsplitter 1002 and is prevented from being incident to the sensor 1007. The light scattered by the short-circuit defect or the open-circuit defect has a different angle of polarization from the light scattered by edge roughness, which enables the light scattered by the short-circuit defect or the open-circuit defect to transmit to the polarization beamsplitter 1002 and reach the sensor 1007. Because the short-circuit defect and the open-circuit defect are left in the optical image captured by the sensor 1007 while light-dark unevenness caused by the edge roughness is removed, the short-circuit defect and the open-circuit defect is easily inspected in the optical image. That is, the pattern of the optical resolution limit or less can be inspected using the optical image captured by the sensor 1007.

The Faraday rotation angle $\theta$ is changed as follows.

As illustrated in FIGS. 2 and 3, the Faraday rotator 1004 includes the optical material 1004a and the coil 1004b wound around the optical material 1004a. The intensity of the magnetic field applied to the optical material 1004a is controlled by changing the current passed through the coil 1004b, which allows the Faraday rotation angle $\theta$ to be changed. At this point, the Faraday rotation angle $\theta$ is expressed by the following equation. Where H is the intensity of the magnetic field, l is a length of a substance transmitting the polarized light, and V is called a Verdet constant that depends on a kind of the substance, the wavelength of the polarized light, and temperature.

$\theta = VHl$

For example, in the case that a material, such as $SiO_2$, $CaF_2$, and $MgF_2$, which has the high transmittance to the DUV light is used as the optical material 1004a, because the material does not have spontaneous magnetization, it is necessary to apply the large magnetic field to the optical material 1004a in order to obtain the desired Faraday rotation angle $\theta$.

The Faraday rotation angle $\theta$ that properly separates the light scattered by the short-circuit defect or the open-circuit defect from the light scattered by the edge roughness depends on the pattern structure. For this reason, in the inspection apparatus 100, the Faraday rotation angle $\theta$ is changed according to the pattern of the sample 1. Specifically, an angle control circuit 14 changes the current passed through the coil of the Faraday rotator 1004, and therefore the intensity of the magnetic field applied to the optical material is changed such that the Faraday rotation angle $\theta$ is obtained according to the type of the pattern.

In the case that the permanent magnet is used in the Faraday rotator, multiple permanent magnets having different intensities of the magnetic field are prepared. The permanent magnet is selected such that the Faraday rotation angle $\theta$ is obtained according to the type of the pattern, and the magnetic field necessary for the optical material is applied.

The Faraday rotation angle $\theta$ is also changed by changing a thickness of the optical material. Accordingly, multiple optical materials having different thicknesses are prepared, and the optical material that can achieve the Faraday rotation angle $\theta$ corresponding to the type of the pattern may be selected. In this case, the intensity of the magnetic field applied to the optical material can be uniformed irrespective of the Faraday rotation angle provided to the light.

For example, when the sample 1 is irradiated with the light having the polarization plane of 45 degrees with respect to the repetitive direction of the repetitive pattern formed in the sample 1, a difference between the large defect such as the short-circuit defect and the open-circuit defect and the small defect such as the edge roughness can emerge in the sensitivity to the electric field component of the light. On the other hand, when the sample 1 is irradiated with the light having the polarization plane of 0 degree or 90 degrees with respect to the repetitive direction of the repetitive pattern formed in the sample 1, the large defect and the small defect cannot be distinguished from each other because the large defect is equal to the small defect in the light sensitivity. That is, the polarization plane of the light with which the pattern is illuminated is not necessarily 45 degrees with respect to the repetitive direction of the repetitive pattern, but it is necessary that the polarization plane of the light not be 0 degrees or 90 degrees with respect to the repetitive direction of the repetitive pattern. In other words, preferably the polarization plane of the light is set to any angle except an angle in the range of −5 degrees to 5 degrees and the range of 85 degrees to 95 degrees.

Figure 13:
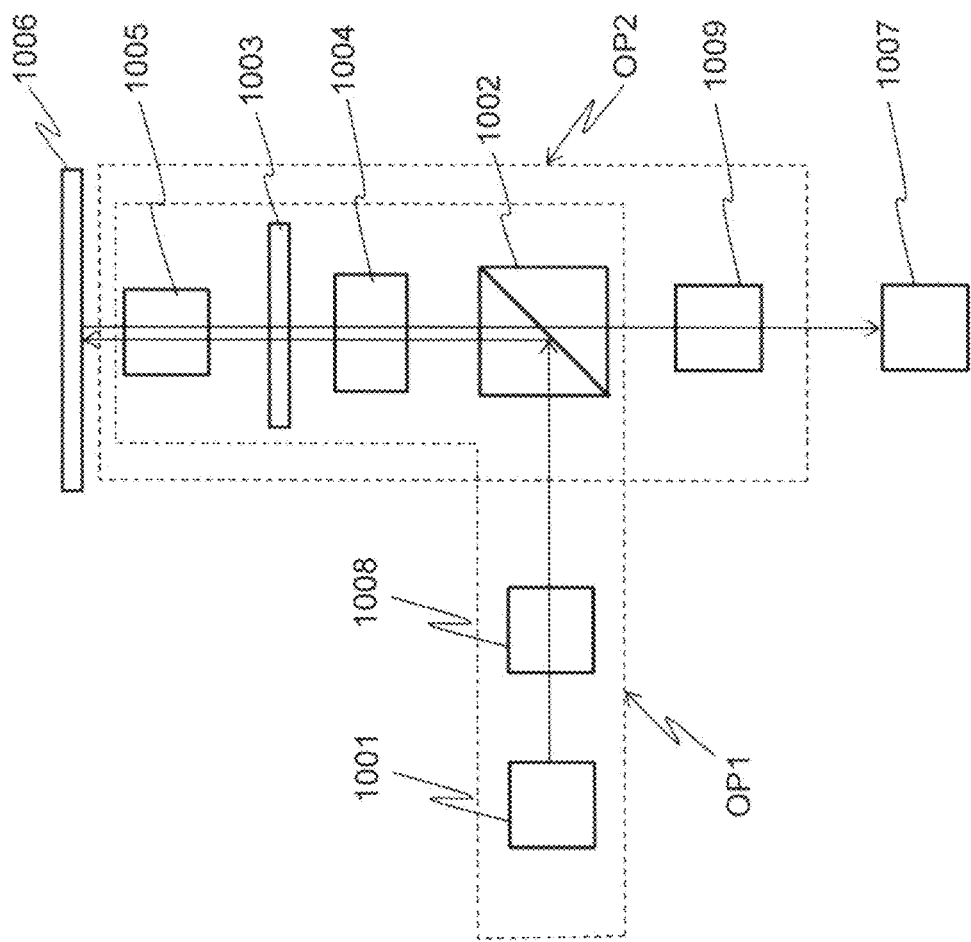
FIG. 13 illustrates another example of a configuration of an image capturing device according to the present embodiment.

The polarization direction of the light with which the mask 1006 is illuminated is changed by not only the Faraday rotator 1004 but also the half-wavelength plate 1003. In the present embodiment, preferably the rotation mechanism is provided in the half-wavelength plate 1003 to rotate the polarization plane of the light at any angle. As shown in FIG. 13, the half-wavelength plate 1003 may be arranged between the Faraday rotator 1004 and the mask 1006, specifically between the Faraday rotator 1004 and the objective lens 1005.

Next, the control unit B as shown in FIG. 5 will be described.

In the control unit B, a control computer 110 that controls the whole inspection apparatus 100 is connected to a position circuit 107, a image processor 108, an angle control circuit 14, a defect detection circuit 134 as a defect detector, an auto-loader control circuit 113, a XY-Table control circuit 114a, Z-Table control circuit 114b, a magnetic disk device 109, a magnetic tape device 115, and flexible disk device 116, which are examples of a storage device, a display 117, a pattern monitor 118, and a printer 119 through a bus 120 that constitutes a data transmission line.

In FIG. 5, the "circuit" is also expressed as the "unit". For example, the image processor 108 corresponds to an image processor of the present invention, and the angle control circuit 14 corresponds to an angle controller of the present invention, further the defect detection circuit 134 corresponds to an a defect detector of the present invention. These components may be constructed with an electric circuit or by a program on a computer. The circuit may also be implemented by not only the program of software but also a combination of hardware and software or a combination of software and firmware. In the case that the circuit is constructed with the program, the program can be recorded in the magnetic disk device 109. For example, each circuit in FIG. 5 may be constructed with the electric circuit or the software that can be processed by the control computer 110. Each circuit in FIG. 5 may be constructed with the combination of the electric circuit and the software. As a more specific example, the defect detection circuit 134, as a detector, may be an apparatus construction, or may be implemented as a software program, or may be implemented as a combination of software and firmware, or software and hardware.

The Z-Table 2 is driven by the motor 17b controlled by the Z-Table control circuit 114b. The XY-Table 3 is driven by the motor 17a controlled by the XY-Table control circuit 114a. For example, a stepping motor is used as each motor.

Next, an example of an inspection method using the inspection apparatus 100 will be described.

An example of a specific method for acquiring the optical image of the sample 1 will be described below.

The sample 1 is placed on the Z-Table 2 that is movable in the perpendicular direction. The Z-Table 2 is provided on the XY-Table 3, and the sample 1 is movable in the horizontal direction and the vertical direction by moving the XY-Table 3. A moving position of the XY-Table 3 is measured by the laser length measuring system 122, and sent to the position circuit 107. The sample 1 on the XY-Table 3 is automatically conveyed from the autoloader 130 that is driven by the auto-loader control circuit 113, and the sample 1 is automatically discharged after the inspection is ended.

The light source 1001 emits the light with which the sample 1 is illuminated. The linearly-polarized light emitted from the light source 1001 is reflected by the polarization beamsplitter 1002, transmitted through the half-wavelength plate 1003, and is incident to the Faraday rotator 1004. The light transmitted through the Faraday rotator 1004 is imaged onto the sample 1 through the objective lens 1005. A distance between the objective lens 1005 and the sample 1 can be adjusted by vertically moving the Z-Table 2.

Then, the light reflected by the sample 1 is transmitted through the objective lens 1005, the Faraday rotator 1004, the half-wavelength plate 1003, and the polarization beamsplitter 1002, and is incident to the sensor 1007. The sensor 1007 captures the optical image of the mask 1006.

Figure 11:
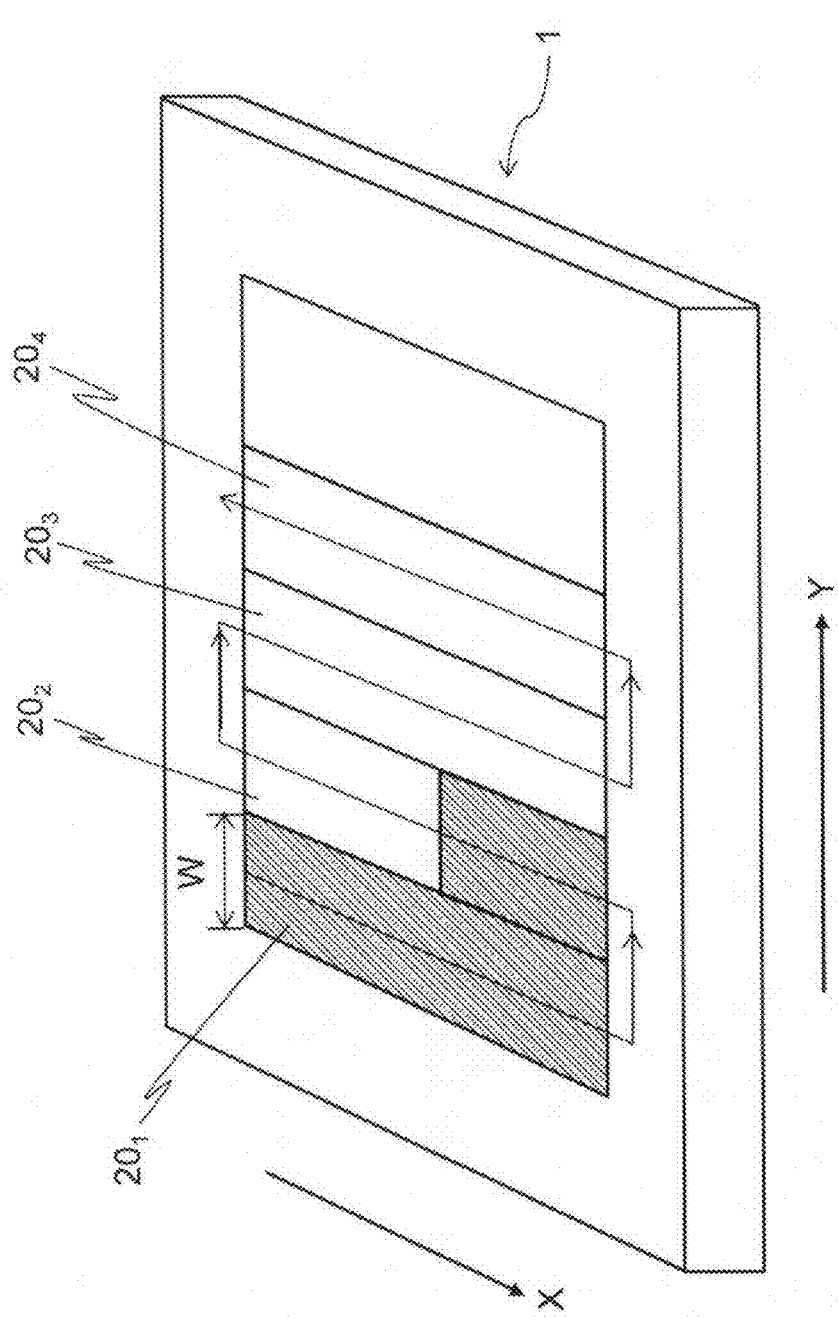
FIG. 11 is a view illustrating a procedure to acquire the optical image of a sample.

FIG. 11 is a view illustrating a procedure to acquire the optical image of the pattern formed in the sample 1.

As illustrated in FIG. 11, an inspection region on the sample 1 is virtually divided into plural strip-like frames $20_1$, $20_2$, $20_3$, $20_4$, . . . . The XY-Table control circuit 114a controls motion of the XY-Table 3 in FIG. 5 such that the frames $20_1$, $20_2$, $20_3$, $20_4$, . . . are continuously scanned. Specifically, the images having a scan width W in FIG. 11 are continuously input to the sensor 1007 while the XY-Table 3 moves in the −X-direction.

That is, after the image of the first frame $20_1$ is captured, the image of the second frame $20_2$ is captured. In this case, the optical image is captured while the XY-Table 3 moves in the opposite direction (X-direction) to the direction in which the image of the first frame $20_1$ is captured, and the images having the scan width W are continuously input to the sensor 1007. In the case that the image of the third frame $20_3$ is captured, the XY-Table 3 moves in the opposite direction (−X-direction) to the direction in which the image of the second frame $20_2$ is captured, namely, the direction in which the image of the first frame $20_1$ is captured. A hatched-line portion in FIG. 11 schematically expresses the region where the optical image is already captured in the above-mentioned description.

After the pattern images formed in the sensor 1007 are subjected to photoelectric conversion, the sensor circuit 106 performs A/D (Analog to Digital) conversion to the pattern images. Image sensors are arranged in the photodiode array 105. As for the sensor 1007 a line sensor, in which CCD cameras as imaging devices are arranged in line, can be used, as one example. The line sensor includes a TDI (Time Delay Integration) sensor. A pattern of the sample 1 is imaged by the TDI sensor while the XY-table 3 continuously moves in the X-axis direction.

The optical image data, to which the sensor circuit 106 performs the A/D conversion after the image capturing with the sensor 1007, is sent to the image processor 108. In the image processor 108, the optical image data is expressed by the gradation value of each pixel. For example, one of values of a 0 gradation value to a 255 gradation value is provided to each pixel using a gray scale having 256-level gradation value. The optical image data sent to the image processor 108 from the sensor 1007 through the sensor circuit 106 is used to inspect the pattern of the optical resolution limit or less in the sample 1.

In the image processor 108, the Faraday rotation angle θ of the Faraday rotator 1004 is set such that the light scattered by the edge roughness in the light from the sample 1 is prevented from being incident to the sensor 1007. Then, the result is sent to the angle control circuit 14, the angle control circuit 14 changes the current passed through the coil of the Faraday rotator 1004, and therefore the intensity of the magnetic field applied to the optical material is changed such that the Faraday rotation angle θ set by the image processor 108 is obtained. At this point, when the sample 1 is illuminated with the light emitted from the light source 1001 again, the light scattered by the short-circuit defect or the open-circuit defect is incident to the sensor 1007 through the half-wavelength plate 1003 and the polarization beam-splitter 1002 while separated from the light scattered by the edge roughness. As a result, in the optical image captured by the sensor 1007, the short-circuit defect and the open-circuit defect are left while the light-dark unevenness caused by the edge roughness is removed. Accordingly, the use of the optical image can inspect the short-circuit defect and the open-circuit defect, namely, the pattern of the optical resolution limit or less.

A specific method for finding the condition that removes the bright and dark unevenness caused by the edge roughness will be described below.

Generally many pieces of edge roughness exist in the whole surface of the mask or template of the inspection target while very few number of short-circuit defects or open-circuit defects exist in the mask or template. For example, when the optical image having the region of 100×100 μm is acquired, there is a low possibility that the short-circuit defect or the open-circuit defect is included in the region, and the very few defects exist in the region even if the short-circuit defect or the open-circuit defect is included in the region. That is, almost all the optical images in the region are caused by the edge roughness. This means that the condition that removes the defect caused by the edge roughness is obtained from one optical image having the size of about 100 μm×about 100 μm.

As mentioned above, the change in gradation value caused by the edge roughness in the optical image can be removed by controlling the polarization direction of the light incident to the sensor 1007 on the imaging optical system side. Specifically, the quantity of light that is incident to the sensor 1007, while being scattered by the edge roughness, is changed by controlling the Faraday rotation angle θ using the Faraday rotator 1004, which allows the bright and dark amplitude to be changed in the optical image.

The bright and dark amplitude in the optical image is expressed by a standard deviation of the gradation value in each pixel. For example, assuming that the optical system (described in FIG. 1) has a pixel resolution of 50 nm in the inspection apparatus 100 in FIG. 5, the optical image having the region of 100 μm×100 μm is expressed by 4 million pixels. That is, a specimen of 4 million gradation values is obtained from the one optical image.

For a dark-field illumination system, the standard deviation is obtained with respect to the specimen, the obtained standard deviation is defined as a degree of the scattering light caused by the edge roughness, and the polarization state on the imaging optical system side, namely, the Faraday rotation angle θ is adjusted such that the standard deviation becomes the minimum. Therefore, the quantity of scattering light incident to the sensor 1007 due to the edge roughness can be minimized.

For the optical image in a bright-field optical system, a degree of the brightness and darkness caused by the edge roughness is influenced by zero-order light. The reason is as follows. Because the fine periodic pattern of the optical resolution limit or less exists in the inspection target, the polarization state of the zero-order light changes due to a phase-difference effect caused by structural birefringence. Therefore, the light quantity that becomes a base also changes when the Faraday rotation angle is changed in order to remove the reflected light caused by the edge roughness. Because the bright-field image is a product of an electric field amplitude of the scattering light from the short-circuit defect, the open-circuit defect, or the edge roughness and an electric field amplitude of the zero-order light, the degree of the brightness and darkness caused by the edge roughness is influenced by an intensity of the zero-order light.

In order to remove the influence of the scattering light due to the edge roughness to improve the detection sensitivity for the short-circuit defect or open-circuit defect, it is necessary to find, not the condition in which a function (specifically, a function expressing the electric field amplitude of the zero-order light) caused by the zero-order light becomes the minimum, but the condition that a function (specifically, a function expressing the electric field amplitude of the scattering light caused by the edge roughness) caused by the edge roughness becomes the minimum. The reason the function caused by the zero-order light becomes the minimum is that the function caused by the zero-order light is the condition that the base light quantity simply becomes the minimum but the influence of the edge roughness is not completely removed.

The function caused by the edge roughness becoming the minimum is obtained by a calculation using a standard deviation σ of the gradation value of the optical image and an average gradation value A. The standard deviation σ includes various noise factors, and particularly the standard deviation σ is largely influenced by the brightness and darkness caused by the edge roughness. The average gradation value A of the optical image is the base light quantity, namely, the intensity of the zero-order light. The electric field amplitude of the scattering light due to the edge roughness is proportional to a value in which the standard deviation σ of the optical image is divided by a square root of the average gradation value A. In order to find the condition that minimizes the bright and dark amplitude caused by the edge roughness, the optical image is acquired while the angle θ of the half-wavelength plate 1007 is changed, and the value ($\sigma/\sqrt{A}$) in which the standard deviation of the gradation value in the obtained optical image is divided by the square root of the average gradation value is calculated. The angle θ is obtained when the value ($\sigma/\sqrt{A}$) becomes the minimum.

As mentioned above, for the large defect such as the short-circuit defect and the open-circuit defect, the vertical direction and the horizontal direction differ from each other in the sensitivity to the electric field component of the illumination light. Accordingly, when the electric field amplitude of the scattering light caused by the large defect becomes the minimum, the Faraday rotation angle θ differs from that of the scattering light caused by the edge roughness. That is, even if the Faraday rotation angle θ is applied when the electric field amplitude of the scattering light caused by the edge roughness becomes the minimum, the electric field amplitude of the scattering light caused by the short-circuit defect or the open-circuit defect does not become the minimum. Therefore, the short-circuit defect and the open-circuit defect can be detected without being buried in the amplitude of the brightness and darkness caused by the edge roughness.

As described above the Faraday rotation angle θ that properly separates the light scattered by the short-circuit defect or the open-circuit defect from the light scattered by the edge roughness depends on the pattern structure. The detail is described as follows.

When the electric field amplitude of the scattering light caused by the edge roughness becomes the minimum, the Faraday rotation angle θ depends on a structure of the pattern formed in the inspection target. For example, Faraday rotation angle θ at which the electric field amplitude of scattering light caused by edge roughness becomes the minimum also changes when a pitch, a depth, or a line and space ratio of the pattern changes. Accordingly, it is necessary to obtain the Faraday rotation angle θ according to the structure of the pattern of the inspection target. In the case that the identical pattern is provided in all inspection targets, the previously obtained angle θ can continuously be used. On the other hand, in the case that the patterns of inspection targets vary from one target to another target, it is necessary to change the Faraday rotation angle θ according to the inspection target. Additionally, even in the identical design pattern, the depth or the line and space ratio is slightly changed by various error factors, and possibly the Faraday rotation angle θ of the half-wavelength plate 1007, which minimizes the electric field amplitude of the scattering light, varies from one target to another target. In this case, it is necessary to follow the variation to change the Faraday rotation angle θ for each individual inspection target, even if the inspection target has an identical pattern.

Thus, the condition that removes the bright and dark unevenness caused by the edge roughness, namely, the angle of the Faraday rotation angle θ can be obtained. This processing is performed at a stage prior to the inspection of the sample 1. That is, in order to find the condition that removes the defect caused by the edge roughness, the sensor 1007 captures the optical image of the sample 1 while the angle of the Faraday rotation angle θ is changed. Specifically, the angle control circuit 14 changes the current passed through the coil 1004b of the Faraday rotator 1004, and therefore the intensity of the magnetic field applied to the optical material is changed such that the predetermined Faraday rotation angle θ is obtained.

For example, one optical image having the size of about 100 μm×about 100 μm may be obtained in each predetermined value of the Faraday rotation angle θ. The generated data of the optical image is sent to the image processor 108 through the sensor circuit 106, and the Faraday rotation angle θ of the Faraday rotator 1004 is set such that the light scattered by the edge roughness in the light from the sample 1 is prevented from being incident to the sensor 1007.

As described above, the optical image data is expressed by the gradation value of each pixel in the image processor 108. Therefore, in the dark-field illumination system, the standard deviation is obtained with respect to one optical image, the obtained standard deviation is defined as the degree of the scattering light caused by the edge roughness, and the Faraday rotation angle θ is obtained such that the standard deviation becomes the minimum. On the other hand, in the bright-field illumination system, the image processor 108 obtains the standard deviation σ and the average gradation value A of the gradation value. The optical image is acquired while the Faraday rotation angle θ is changed, the value in which the standard deviation σ of the gradation value in the acquired optical image is divided by the square root of the average gradation value A is calculated, and the Faraday rotation angle θ is obtained when the value becomes the minimum.

Information on the Faraday rotation angle θ obtained by the image processing circuit 108 is sent to the angle control circuit 14. The angle control circuit 14 controls the current passed through the coil 1004b of the Faraday rotator 1004 according to the information from the image processing circuit 108. Therefore, the intensity of the magnetic field applied to the optical material of the Faraday rotator 1004 can be changed to set the Faraday rotation angle A to the value obtained by the image processing circuit 108.

The Faraday rotation angle A is set to the value obtained by the image processing circuit 108, whereby the light scattered by the edge roughness is prevented from being incident to the sensor 1007. Therefore, the light scattered by the short-circuit defect or the open-circuit defect is incident to the sensor 1007 through the half-wavelength plate 1003 and the polarization beamsplitter 1002 while separated from the light scattered by the edge roughness. In the optical image captured by the sensor 1007, the short-circuit defect and the open-circuit defect are left while the light-dark unevenness caused by the edge roughness is removed. Accordingly, the use of the optical image can inspect the short-circuit defect and the open-circuit defect, namely, the pattern of the optical resolution limit or less.

In the image processor 108, the image data in the optical image (in which the defect caused by the edge roughness is removed) is expressed by the gradation value of each pixel.

The information on the gradation value obtained by the image processor 108 is sent to the defect detection circuit 134. When the short-circuit defect or the open-circuit defect exists in the repetitive pattern of the optical resolution limit or less of the optical system, an irregularity is generated in the regularity of the pattern, the gradation value in the location where the defect exists varies from the surrounding gradation value. Therefore, the short-circuit defect or the open-circuit defect can be detected. Specifically, for example, the defect detection circuit 134 has thresholds above and below the average gradation value, and the location is recognized as the defect when the gradation value sent from the image processor 108 exceeds the threshold. The threshold level is set in advance of the inspection. For example, the defect information obtained by the defect detection circuit 134 is stored in the magnetic disk device 109.

The inspection apparatus 100 can also have a review function in addition to the inspection function. As used herein, the review means an operation in which an operator determines whether the detected defect becomes a problem.

For example, a coordinate of a place determined to be the defect by the defect detection circuit 134 and the optical image are sent to a review tool (not illustrated). An operator reviews the optical image by comparison with a standard image that is a model image. The defect information determined by the review can be stored as a defect information list in the magnetic disk device 109. For example, a reference image produced by design data of the inspection target pattern is used as the standard image.

According to the present embodiment, the use of the combination of the polarization beamsplitter and the Faraday rotator instead of the half mirror provides the image capturing device that can minimally restrain the degradation of the light quantity in the reflected illumination optical system to capture the image of the object. The use of the image capturing device provides the inspection apparatus and inspection method, for being able to minimally restrain the degradation of the light quantity in the reflected illumination optical system to capture the image of the inspection target, which allows the inspection to be performed with high accuracy.

According to the present embodiment, the pattern of the optical resolution limit or less can be inspected by changing the Faraday rotation angle θ. That is, according to the inspection apparatus and inspection method of the present embodiment, the fine pattern can accurately be inspected without generating the throughput degradation.

The present invention is not limited to the embodiment described and can be implemented in various ways without departing from the spirit of the invention.

In the above embodiments, the sample is illuminated with the light emitted from the light source, and the light reflected from the sample is incident to the sensor to capture the optical image. Alternatively, the light transmitted through the sample may be incident to the sensor to capture the optical image. The above description of the present embodiment has not specified apparatus constructions, control methods, etc., which are not essential to the description of the invention, since any suitable apparatus construction, control methods, etc. can be employed to implement the invention. Further, the scope of this invention encompasses all image capturing devices, inspection apparatus and inspection methods employing the elements of the invention and variations thereof, which can be designed by those skilled in the art.

What is claimed is:

1. An image capturing device comprising:
a light source configured to emit light having a predetermined wavelength;
a polarization beamsplitter configured to reflect the light from the light source;
a Faraday rotator having an optical material configured to rotate a polarization plane of the light reflected from the polarization beamsplitter by changing intensity of a magnetic field or changing the thickness of the optical material;
an objective lens configured to illuminate an inspection target with the light transmitted through the Faraday rotator;
a sensor configured to capture an optical image of the inspection target by causing the light reflected by the inspection target to be incident through the objective lens, the Faraday rotator, and the polarization beamsplitter;
an image processor configured to obtain a gradation value in each pixel with respect to the optical image and acquire (a) a rotation angle of the polarization plane of the light rotated by the Faraday rotator for minimizing a standard deviation of the gradation value, or (b) a rotation angle for minimizing a value which is obtained by dividing the standard deviation of the gradation values of a plurality of optical images obtained by changing the rotation angle, by a square root of an average gradation value obtained from the gradation value, wherein a rotation angle of the Faraday rotator is adjusted to the rotation angle acquired by the image processor; and
a defect detector configured to detect a defect of the inspection target based on an optical image which is captured while the magnetic field is applied to the Faraday rotator.

2. The image capturing device according to claim 1, wherein the Faraday rotator rotates a polarization plane of the light before the transmission through the Faraday rotator such that the polarization plane rotates 90 degrees by transmitting the light back and forth through the Faraday rotator, by applying the magnetic field.

3. The image capturing device according to claim 2, wherein the Faraday rotator includes an optical material that transmits the light, and
the magnetic field is applied to the optical material by one selected from a group consisting of an electromagnet, a permanent magnet, and a combination of the electromagnet and permanent magnet.

4. The image capturing device according to claim 1, further comprising: a half-wavelength plate configured between the polarization beamsplitter and the inspection target,
wherein the half-wavelength plate changes a polarization direction of the light with which the inspection target is illuminated.

5. The image capturing device according to claim 4, wherein the half-wavelength plate is configured between the polarization beamsplitter and the Faraday rotator.

6. The image capturing device according to claim 4, wherein the half-wavelength plate is configured between the Faraday rotator and the inspection target.

7. The image capturing device according to claim 4, wherein the half-wavelength plate includes a rotation mechanism, and
the rotation mechanism changes the polarization direction of the light by changing an angle of the half-wavelength plate.

8. The image capturing device according to claim 1, wherein the predetermined wavelength of the light from the light source and a numerical aperture of an objective lens defines a resolution limit, wherein the resolution limit is a value at which a repetitive pattern formed in the inspection target is not resolved.

9. The image capturing device according to claim 1, wherein a plurality of permanent magnets having different intensities of the magnetic field are prepared for the Faraday rotator, and
wherein the rotation angle of the Faraday rotator is adjusted by selecting appropriate one of the plurality of permanent magnets so as to obtain the rotation angle acquired by the image processor.

10. The image capturing device according to claim 1, wherein a plurality of optical materials having different thicknesses are prepared for the Faraday rotator,
wherein the rotation angle of the Faraday rotator is adjusted by selecting appropriate one of the plurality of optical materials so as to obtain the rotation angle acquired by the image processor.

11. The image capturing device according to claim 1, wherein a coil through which an electric current passes to generate the magnetic field is provided in the Faraday rotator,
wherein the rotation angle of the Faraday rotator is adjusted by controlling the current so as to obtain the rotation angle acquired by the image processor.

* * * * *